United States Patent [19]

Fischetti et al.

[11] Patent Number: 5,786,205
[45] Date of Patent: Jul. 28, 1998

[54] DELIVERY AND EXPRESSION OF A HYBRID SURFACE PROTEIN BY BACTERIA

[75] Inventors: Vincent A. Fischetti, West Hempstead; Olaf Schneewind, New York, both of N.Y.

[73] Assignee: The Rockefeller University, New York, N.Y.

[21] Appl. No.: 735,670

[22] Filed: Oct. 17, 1996

Related U.S. Application Data

[63] Continuation of Ser. No. 280,390, Jul. 26, 1994, Pat. No. 5,616,686, which is a continuation of Ser. No. 46,495, Apr. 8, 1993, abandoned, which is a continuation of Ser. No. 902,432, Jun. 18, 1992, abandoned, which is a continuation of Ser. No. 814,323, Dec. 23, 1991, abandoned, which is a continuation of Ser. No. 742,199, Aug. 5, 1991, abandoned, which is a continuation of Ser. No. 522,440, May 11, 1990, abandoned.

[51] Int. Cl.$^6$ .................... C07H 21/04; C12N 15/00; C12N 1/20
[52] U.S. Cl. .................... 435/252.3; 435/252.33; 435/252.8; 435/320.1; 435/325; 536/23.5; 536/23.7
[58] Field of Search .................... 536/23.7, 23.5; 435/320.1, 252.3, 252.33, 252.8, 325

[56] References Cited

U.S. PATENT DOCUMENTS 4,784,948  11/1988  Scott et al. .

OTHER PUBLICATIONS

Lazar et al (Molecular & Cellular Biology vol. 8 No. 3 pp. 1247–1252, Mar. 1988.

Burgess et al (J. of Cell Biology vol. 111 pp. 2129–2138, Nov. 1990.

Salgaller et al (Cancer Immunol. Immunother. vol. 39 pp. 105–116, 1994.

Hollingshead et al (J. of Biological Chem. v.261 No. 4 pp. 1677–1686, 1986.

*Primary Examiner*—Anthony C. Caputa
*Assistant Examiner*—Mark Navarro
*Attorney, Agent, or Firm*—Burns, Doane, Swecker & Mathis, L.L.P.

[57] ABSTRACT

Process is described for the delivery and expression of hybrid surface proteins to the surface of bacteria. The transformed bacteria are useful as vaccines, for the delivery of other active peptides to animal hosts, as diagnostic reagents, and for other purposes.

11 Claims, 2 Drawing Sheets

```
M6        (375)   PGNKVVPGKGQAPQAGTKPNQNKAPMKETKRQLPSTGETANPFFTAAALTVMATAGVAAVVKRKEEN
wapA      (382)   QTKTTASQTNVPTTNITTSKQVTKQKAKFVLPSTGEQAGLLLTTVGLVIVAVAGVYFYRTRR
M49       (283)   ELAKLKGNQTPNAKVAPQANRSRSAMTQQKRTLPSTGETANPFFTAAAATVMVSAGMLALKRKEEN
IgA-BP    (280)   ELAKLKGNQTPNAKVAPQANRSRSAMTQQKRTLPSTGETANPFFTAAAATVMVSAGMLALKRKEEN
Fc-BP     (359)   PDTKPGNKEVPTRPSQTRTNTNKAPMAQTKRQLPSTGEETNPFFTA·
Protein A (422)   KLADKNMIKPGGELVVDKKQPANHADANKAQALPETGEENPLIGTTYVFGGLSLALGAALLAGRRREL
Protein G (494)   PIAKDDAKKDDTKKEDAKKPEAKKDDAKKAETLPTTGEGSNPFFTAAALAVMAGAGALAVASKRKED
Fn-BP     (904)   VEQGKVVTPVIEINEKVKAVAPTKKPQSKKSELPETGGESTNKGMLFGGLFSILGLALLRRNKKNHKA
T6        (472)   KALTDGTTFSKSNEGSGTVLLETDIPNTKLGELPSTGSIGTYLFKAIGSAAMIGAIGIYIVKRRKA
Pac       (1496)  TDPQDPSSPRTSTVIIYKPQSTAYQPSSVQETIPNTGVINNAYMPLLGIIGLVTSFSLLGLKAKKD
Wg2       (1835)  GGNIPTNPATTSTSTDDTTDRNGQLTSGKGALPKTGETERPAFGFLGVIVILMGVLGLKRKQREE
```

FIG. 2A

```
              L P (S) T G (E)
M6        CCAATGAAGGAAACTAAGAGACAGTTACCATCAACAGGTGAAACAGCTAACCCATTCTTCACAGCG
wapA      A-C-A-C-AA---A-G-G--ATTTGT----A-------CA----AGGG-TT--G--A--TA--T
M49       -A--AT--A-G--TG-GATC----A-------G-----C-------GA-A--A-C-AACCCA----T
IgA-BP    G--------CAC---CAA----AC--------G-----C-------GA-AA--CCATTCA--GGT--A--T
Fc-BP     --T---GC-C---A------A--------------G-----C-------GA-A--C--AACCCA---TTCA---T
Protein A G--GATGCTA-C--AAGCTCA-GCA------GA---T--C--GA--AA-CCATTCA--GGT---A--T
Protein G GA--GACGCTA-G--AAGCTGA-ACTC-T---GA---T--TA--------GG--AGC--------A
Fn-BP     AA--CCAC-ATCT--AG---ATCTG-AC----TGA---------G-GA--AATCAA--CTTACC--T-A--T
T6        ATCCCT---CACC-AGCTAG-TG-A-------T--G-----AAT--G-AT---G---AAC--TG-T-ATA-GC-TTTA
Pac       --AGCCA--GCTCTGT-C-AGA-ACA------CAAG---A---G-------A---G---GGCCAGGTTT--GC
Wg2       --A-C--T-CATCCGG-----G--GCA----------------------------------------
```

FIG. 2B

DELIVERY AND EXPRESSION OF A HYBRID SURFACE PROTEIN BY BACTERIA

This application is a continuation of application Ser. No. 08/280,390, filed Jul. 26, 1994, now U.S. Pat. No. 5,616, 686, which is a continuation of Ser. No. 08/046,495, filed Apr. 8, 1993 now abandoned, which is a continuation of Ser. No. 07/902,432, filed Jun. 18, 1992 now abandoned, which is a continuation of Ser. No. 07/814,323, filed Dec. 23, 1991, now abandoned, which is a continuation of Ser. No. 07/742, 199, filed Aug. 5, 1991, (now abandoned) which is a continuation of Ser. No. 07/522,440, filed May, 11, 1990 now abandoned.

BACKGROUND OF THE INVENTION

This invention relates to polypeptides which, like antibiotics, can be employed to inhibit the spread of bacterial infections in mammals caused by gram-positive bacteria.

One aspect of the structure of gram-positive bacteria including, for example, bacteria such as streptococci and staphylococci which are responsible for such mammalian infections as strep throat, rheumatic fever, nephritis, toxic shock syndrome and endocarditis is the presence of virulence determinants responsible for infecting the host cell. These determinants are essential factors for the spread of infection following any of a number of mechanisms known to those skilled in the art. They may take the form of enzymes, anti-phagocytotic agents, adhesive molecules and others. One form of virulence determinant is the M-protein which is a protein attached to the surface of gram-positive streptococci. The streptococcal M-protein is a coiled-coil fibrillar structure extending about 60 nm from the streptococcal cell wall.

This invention arises from structural studies of the M protein and other virulence determinants located on the surface of gram positive bacteria and the mechanisms by which such surface proteins are anchored to the cell.

FIG. 1 is a schematic representation of the coiled-coil M protein molecule on the streptococcal cell wall. The molecule which comprises approximately 441 amino acid residues is shown with a variable amino end and a conserved carboxyl end, the so called N-terminal and C-terminal. The protein is shown as extending from the outer surface of the cell. The surface of the cell comprises the cell membrane and the cell wall which is composed of peptidoglycan and group carbohydrate. The N-terminal end of the molecule is more exposed to the immune system, and the variability of the N-terminal region is the principal reason why there is difficulty in preparing a vaccine effective against all strains of streptococci.

This invention is principally concerned with that region of the C-terminal of the M-protein which, in FIG. 1, is shown at the interface between the cell wall and the cell membrane and penetrating into the cell membrane.

Surface proteins in both gram-positive and gram-negative bacteria are generated in the cytoplasm, transferred through the membrane and anchored at their C-terminal ends to the membrane. If the anchor is missing the protein will escape into the growth media with gram-positive bacteria. In gram-negative bacteria, the protein becomes trapped in the periplasmic space between the cell wall and the outer membrane.

To understand the basis for this invention, it is necessary to consider in some detail the structure of the C-terminal of the M-protein and to understand from these considerations the nature of the anchoring mechanism of the M-protein to the cell surface.

FIG. 2A shows in the first line of the top section the amino acid sequence of the M6-protein from position 375 to 441 at the C-terminal. It also shows in subsequent lines the amino acid sequences at the C-terminal of several other gram-positive bacteria, the significance of which will become apparent as the discussion progresses.

The lower portion of FIG. 2B shows the oligonucleotide structure of selected portions of each of the genes which express the polypeptides shown in the upper section. In the figure, the standard single letter codes are employed to identify the amino acids and the bases.

Attention is directed to the shaded areas of the upper section. It will be noted that in most of the polypeptides shown, the sequence LPSTGE is highly conserved. This observation is most important to the understanding of this invention.

Reading from the leucyl residue (L) at the N-terminal end of the shaded area of FIG. 2A, the C-terminal of the M6 protein is composed of the LPSTGE region; a linker region, TAN; a hydrophobic region of twenty amino acids, PFFTAAALTVMATAGVAAVV; followed by a highly charged tail region, KRKEEN.

It will be noted that in each of the polypeptides shown, which are, in fact, segments of known surface molecules some of which are virulence determinants on the surface of gram-positive bacteria, there is a most highly conserved region, principally LPSTGE, a relatively highly conserved hydrophobic region containing from about 15 to 20 amino acid residues, a charged tail region containing from about 4 to 6 amino acid residues and a linker region joining the LPSTGE region to the hydrophobic region. This linker region contains from about 3 to 7 amino acids.

This homology, of course, reflects comparable conserved regions in the oligonucleotides as shown in the lower part of FIG. 2B.

To study these structures and their importance in designing polypeptides useful to inhibit the spread of infection caused by gram-positive bacteria it was necessary to produce a number of products including genes, plasmids and E. coli vectors carrying the plasmids.

Table I lists several of these plasmids and the characteristic features of the proteins expressed by E. coli carrying each plasmid.

The nature of the proteins was determined by several factors including the genetic structure of the plasmid used to express them, gel electrophoresis using selected markers and antibodies. The details of these studies are given in the experimental section.

Three general types of plasmids were produced. One set based on M6.1, one set based on PIII or PIII fused to M6.1, and a final set based on PhoA or PhoA fused with M6.1. The three basic plasmids and methods for their production are all known. The proteins produced by the expression of the various plasmids are generally characterized by the presence or absence of the LPSTGE region and/or the hydrophobic region.

The various plasmids were expressed from selected strains of E. coli which were then analyzed to determine the position of the expressed protein on the outer cell surface or in the periplasm. The fact that the protein is on the outer surface is established by the experiment described at pages 21, lines 1 through 12. The results of the analysis appear beneath the table.

TABLE 1

| Plasmid | Protein |
|---|---|
| pM6.1 | M6[1] |
| pM6.1$_{1-406}$ | M6 minus LPSTGE, hydrophobic region and charged tail[2] |
| PM6.1$_{\Delta LPSTG}$ | M6 minus LPSTGE, but including the hydrophobic region and the charged tail[3] |
| pNDI | PIII[4] |
| pND372 | PIII gene devoid of its own membrane anchor[5] |
| pPIII:M6.1$_{367-441}$ | Contains LPSTGE, hydrophobic region and charged tail of M6 fused to position 375 of pIII[6] |
| pPIII:M6.1$_{413-441}$ | Contains hydrophobic and tail region of M6 fused to position 375 of PIII, but no LPSTGE region[7] |
| pPhoA | pPhoA protein, with no anchor[8] |
| pPhoA:M6.1$_{303-441}$ | Contains LPSTGE, hydrophobic and tail regions of M6 fused to C-terminal of pHoA[9] |
| pPhoA:M6.1$_{414-441}$ | Contains hydrophobic and tail regions of M6, but no LPSTGE, fused to C-terminal of phOA[10] |

Proteins expressed by these plasmids:

1. Found in membrane fraction.
2. Secreted in periplasm, but not found on membrane.
3. Secreted in periplasm, but not found on membrane.
4. Found in membrane fraction.
5. Secreted in periplasm, but not found on membrane.
6. Found in membrane fraction.
7. Secreted in periplasm, but not found on membrane.
8. Secreted in periplasm, but not found on membrane.
9. Found in membrane fraction.
10. Found in periplasm, but not on membrane.

From a study of these results, it can be concluded that the M protein will attach itself to the cell membrane when both the LPSTGE region and the hydrophobic region are present. The hydrophobic region alone is not sufficient for anchoring. The LPSTGE region, or an analog is responsible for anchoring the M-protein. This invention is based on that discovery.

BRIEF DESCRIPTION OF THE DRAWINGS

FIG. 2 shows the amino acid sequence of the C-terminal end of known surface proteins some of which are virulence determinants of certain gram-positive coccal bacteria (upper section) and portions of the genes which code for selected regions of the sequences (lower section).

SUMMARY OF THE INVENTION

Figure 1:
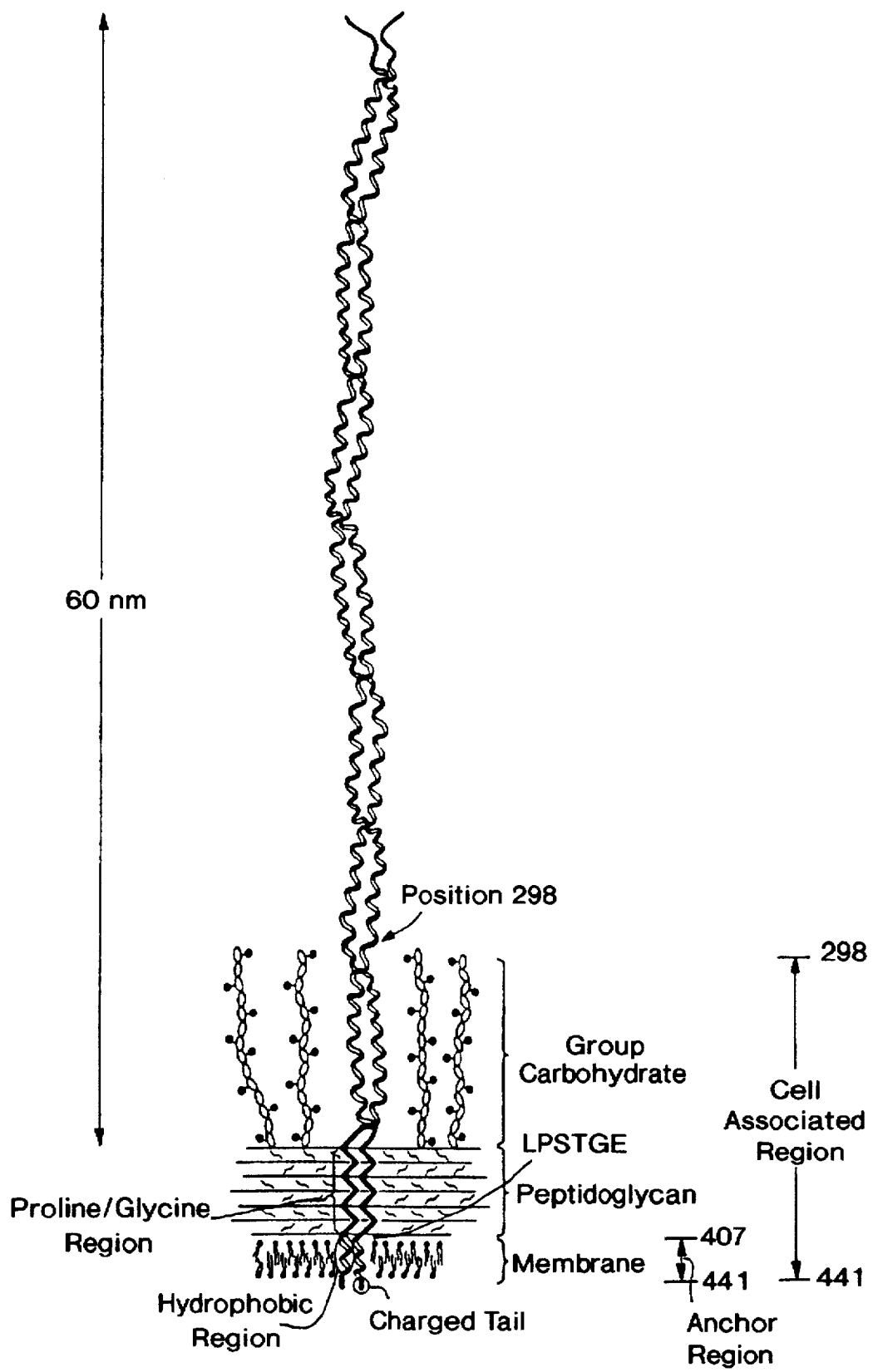
FIG. 1 is a schematic representation of the M-protein showing its relation to the cell wall in a gram-positive streptococcus.

It has now been discovered that polypeptides containing from about 6 to about 20 amino acid residues and including as an integral portion of their structures a peptide construct containing from about 6 to about 10 amino acid residues which is responsible for anchoring a virulence determinant to the surface of a gram positive coccal bacteria, or their pharmaceutically acceptable salts, can be administered to a mammal infected by the bacteria thereby to inhibit the spread of the infection. The invention also includes methods for such administration and pharmaceutically acceptable compositions containing the therapeutic agents.

The invention will be better understood from a consideration of the sequences of the amino acid residues in the shaded areas of FIG. 1. Table 2 shows the hexapeptide sequences found at the C-terminal end of surface proteins from various strains of bacteria.

TABLE 2

| BACTERIA | SURFACE PROTEINS | SEQUENCES |
|---|---|---|
| Streptococcus pyogenes | M6 | LPSTGE |
| Streptococcus mutans | wapA | LPSTGE |
| Streptococcus pyogenes | M49 | LPSTGE |
| Streptococcus pyogenes | IgA-BP | LPSTGE |
| Streptococcus pyogenes | FC-BP | LPSTGE |
| Staphylococcus aureus | Protein A | LPETGE |
| Group G Streptococcus | Protein G | LPTTGE |
| Staphylococcus aureus | Fn-BP | LPETGG |
| Streptococcus pyogenes | T6 | LPSTGS |
| Streptococcus mutans | PAc | LPNTGV |
| Streptococccus cremoris | Wg2 | LPKTGE |

These hexapeptides, as has been pointed out above, are essential for anchoring the proteins to the surface of the cell. Their highly conserved nature is readily apparent. They can be generically represented by the formula:

$$LP(x)TG(y)$$

where x and y represent a limited variety of amino acid residues.

The therapeutic agents can be defined as hexapeptides in which the first, second, fourth and fifth amino residues from the N-terminal are derived from leucine, proline, threonine and glycine, respectively.

It will be noted that the predominant amino acid residues in the three position are the hydroxylated amino acids, serine and threonine. The predominant residue in the six position is glutamic acid. In both instances, other amino acid residues are possible.

The polypeptides of the invention are amphoteric. They can exist and be utilized as free bases or as pharmaceutically acceptable metallic or acid addition salts. Suitable metallic salts include alkali and alkaline earth metal salts, preferably sodium or potassium salts. Acid addition salts may be prepared from a wide variety of organic and inorganic acids including mineral acids, for example citric, lactic, maleic, tartaric, phosphoric and hydrochloric acids. These salts can be prepared by procedures well known to those skilled in the art.

The preferred polypeptide for use in this invention is LPSTGE because it is the most prevalent of the anchoring moieties. Any of the others listed above and their analogs can be similarly employed.

The compounds of this invention are synthesized by standard solid phase procedures with appropriate amino acids using the protection, deprotection and cleavage techniques and reagents appropriate to each specific amino acid or peptide. A combination of manual and automated (e.g., Applied Biosystem 430A) solid phase techniques can be used to synthesize the novel peptides of this invention. Although less convenient, classical methods of peptide synthesis can also be employed. For background on solid phase techniques, reference is made to Andreu, D., Merrifield, R. B., Steiner, H. and Boman, H. G., (1983) Proc. Natl. Acad. Sci USA 80, 6475-6479; Andreu, D., Merrifield, R. B., Steiner, H. and Boman, H. G., (1985) Biochemistry 24, 1683-1688; Fink, J., Boman, A., Boman, H. G., and Merrifield, R. B., (June 1989) Int. J. Peptide Protein Res. 33, 412-421; Fink, J., Merrifield, R. B., Boman, A. and Boman, H. G., (1989) J. Biol. Chem. 264, 6260-6267; each of which being hereby incorporated herein by reference.

It will, normally, be most convenient to administer one or more of the hexapeptides listed above and shown in FIG. 2 to a mammal in need of such treatment. However, those skilled in the art will recognize that other polypeptides containing more amino acid residues, even up to 20 or more such residues can be similarly employed so long as the polypeptide contains as an integral portion of its structure a peptide construct which participates in the anchoring mechanism of the virulence determinant. The selected therapeutic agent may contain, for example all or part of the hydrophobic region at the C-terminal of the determinant. It presently appears to be essential that the anchoring construct contains at least leucyl, prolyl, threonyl and prolyl residues, but it may not need to contain six amino acid residues, especially if it is a construct in a larger polypeptide.

The therapeutic agents of the invention are analogous to antibiotics and, like antibiotics can be used prophylactically to avert infection or may be used to inhibit the spread of an already existing infection. For convenience, both utilities are referred to in this disclosure and claims as "inhibiting" infection.

In general, the therapeutic agents of the invention may be administered orally or parenterally in pure solid form, in dilute solutions or suspensions or in concentrates and prepared for unit dose or multi-dose presentation. When administered parenterally, by intravenous or intramuscular or subcutaneous injection, or when administered orally, the dosage administration will be dependent on the age and weight of the mammalian species being treated, the route of administration, the type and severity of the infectious condition being treated and other factors readily evaluated by the physician or veterinarian in attendance.

In respect to pharmaceutical compositions containing the polypeptides herein, carrier and other ingredients should be such as not to diminish the therapeutic effects of the antibiotic like polypeptides. Suitable dosage forms for oral use are tablets, dispersible powders, granules, capsules, syrups and elixirs. Examples of parenteral forms are solutions, suspensions, dispersions, emulsions, and the like. The compositions for oral use may contain one or more conventional additives such as sweetening agents, flavoring agents, coloring agents and preserving agents, in order to provide a composition of suitable pharmaceutical elegance. Tablets may contain the active ingredient in admixture with conventional pharmaceutically acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated or coated by known techniques to delay disintegration and absorption in the gastrointestinal tract and thereby provide a sustained action over a longer period. Similarly, suspensions, syrups, and elixirs may contain the active ingredients in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl p-hydroxybenzoate. Capsules may contain the active ingredient alone or admixed with an inert solid diluent such as calcium carbonate, calcium phosphate and kaolin. The injectable compositions are formulated as shown in the art and may contain appropriate dispersing or wetting agents and suspending agents identical or similar to those mentioned above.

The usual pharmaceutical carriers for parenteral administrations are isotonic aqueous sodium chloride or glucose solution buffered to a pH of about 7 to 8, normally 7.4. Other pharmaceutically acceptable carriers such as sesame or cottonseed oil may also be employed.

Optimal dosages and regimens for a given mammalian host can be readily ascertained by the physician or veterinarian in attendance. It will, of course, be appreciated that the actual dose will vary according to the particular composition formulated and other factors mentioned above.

While this invention should not be limited by theory, it presently appears that the mode of operation of the peptides of the invention is that, because of their homology to the sequences of the surface virulence determinants in the wild type surface protein, they react with and saturate the enzymes in the membrane necessary for anchoring these determinants. As a result, the virulence determinants of the infecting bacteria are unable to anchor and the infection is unable to spread.

It will be appreciated from all of the above that the basis of this invention is the discovery that an essential aspect of the anchoring mechanism of a virulence determinant which is a protein to the surface of a gram-positive coccal bacteria in the presence of the construct LPSTGE, or one of its analogs defined above, upstream of a hydrophobic region at the C-terminal of the protein. The experiments which lead to this discovery will now be described in some detail. The experiments were conducted in *E. coli* a gram-negative organism rather than in a streptococcus because the procedures are better worked out for *E. coli* than for streptococci and because of the art recognized analogy between cyloptasmic membrane structures of the microorganisms.

In the description, the conventions shown in Table 3 are employed.

TABLE 3

| A | Ala | Alanine |
|---|-----|---------|
| V | Val | Valine |
| L | Leu | Leucine |
| I | Ile | Isoleusine |
| P | Pro | Proline |
| F | Phe | Phenylalanine |
| Y | Tyr | Tyrosine |
| M | Met | Methionine |
| G | Gly | Glycine |
| S | Ser | Serine |
| T | Thr | Threonine |
| C | Cys | Cysteine |
| N | Asn | Asparagine |
| Q | Gln | Glutamine |
| D | Asp | Aspartid acid |
| E | Glu | Glutamic acid |
| K | Lys | Lysine |
| R | Arg | Arginine |
| H | His | Histidine |

Employing these conventions, the presently preferred compositions of the invention are:

1: LPSTGE
Leu-Pro-Ser-Thr-Gly-Glu
Leucyl-Prolyl-Seryl-Threonyl-Glycyl-Glutamic acid 2. LPETGE
   Leu-Pro-Glu-Thr-Gly-Glu
   Leucyl-Prolyl-Glutamyl-Threonyl-Glutamic acid
3. LPTTGE
   Leu-Pro-Thr-Thr-Gly-Glu
   Leucyl-Prolyl-Threonyl-Threonyl-Gluycyl-Glutamic acid
4. LPETGG
   Leu-Pro-Glu-Thr-Glu-Glu
   Leucyl-Prolyl-Glutamyl-Threonyl-Glutamyl-Glutamic acid
5. LPSTGS
   Leu-Pro-Ser-Thr-Glu-Ser
   Leucyl-Prolyl-Seryl-Threonyl-Glutamyl-Serine
6. LPNTGV
   Leu-Pro-Asn-Thr-Gly-Val
   Leucyl-Prolyl-Asparagyl-Threonyl-Glycyl-Valine
7. LPKTGE
   Leu-Pro-Lys-Thr-Gly-Glu
   Leucyl-Prolyl-Lysyl-Threonyl-Glycyl-Glutamic acid

EXPERIMENTAL PROCEDURES

Bacterial Strains

The known *E. coli* K12 strain HMS174(DE3) used for expressing pM6.1, pM6.1$_{-406}$, pM$_{ALPSTGE}$, and all other constructs (1); T7 lysozyme expressing plasmids pLysS and pLysE prepared as described by Studier were present to prevent overexpression by T7 polymerase. Expression of PhoA constructs was performed without induction in *E. coli* HMS174(DE3)(pLysS). The pIII constructs were grown in strain HMS174(DE3)(pLysE); the lacI$_Q$ determinant is required for lacUV5 promotor repression and located on the lysogenic phage (DE3). The lacI$^Q$ *E. coli* K38 strain K561 (2,3) was used for the expression of pND1, pND372, pPIII:M6.1$_{367-441}$ and pPIII: M6.1$_{413-441}$. *E. coli* K12 strain CC118, prepared as described in reference 4, was the host for pphoA; pPhoA:M6.1$_{303-441}$ and pPhoA:M6.1$_{414-441}$ were expressed in strain KS476 (5) both strains are pHoA.

Chemicals and Enzymes

All chemicals were from Sigma unless otherwise described. Restriction enzymes, Klenow polymerase, T4DNA Ligase and HindIII-linker (PCAAGCTTG) were from New England Biolabs. Alkaline Phosphatase was obtained from Boehringer Mannheim. The Sequenase 2.0 kit, United States Biochemicals was used for sequencing reactions. Oligonucleotides were generated by the Protein Sequencing Facility of The Rockefeller University using standard procedures. Cloning procedures are described elsewhere (6).

Polymerase Chain Reaction (PCR) and Plasmid

Construction: The pM6.1 and pPhoA derivatives were constructed by generating polymerase chain reaction (PCR) fragments as described in (U.S. Pat. No. 4,683,202) and subsequent cloning into the known plasmid prepared as described in (7) pT7-5. The M6.1 segment in pPIII:M6.1$_{413-441}$ was also amplified by PCR and cloned into pND372. The correct sequences were confirmed by DNA sequencing as described by Sanger (8).

The pM6.1 derivatives were amplified from pVV:M6Δ described in (9) as a template by using the GeneAmp kit (Perkin Elmer Cetus). All amplifications were performed with 25 temperature cycles 94°–55°–72° C. for 1 min each.

pM6.1: The Eco-primer (AAGAATTCAACATAAGGAGCATAAAAATGGC) was used as upstream primer and the Pst-primer (AACTGCAGAAGAGTTGTTTAGTTTGTGACCT) as a downstream primer; the amplified fragment was cut with EcoRI/PstI and cloned into corresponding restriction sites of pT7-5. This plasmid contains the entire coding sequence for the emm6 gene.

pM6.1 406$_1$:The Eco-primer was employed as with pM6.1 and the Bam1 primer (AAGGATCCCTGTCTCTTAGTTTCCTTCATTG) amplified downstream. The resulting fragment was cut with EcoRI/BamHI and cloned into pT7-5-Stop. This is pT7-5 containing the following sequence between the PstI and HindIII site of pT7-5: CTGCAGTAGCTAGCT-GAGAGCTT which serves as a source for STOP codons (underlined). The plasmid pM6.1$_{1-406}$ codes for the M6 protein from the first through amino acid 406 (i.e. the Q residue before the LPSTGE motif) and has a tail of 8 amino acids from the linker region: GSSRVDLQ. The presence of this extraneous peptide construct does not interfere with the study or affect the conclusions.

pM6.1$_{ALPSTGE}$: The Eco-primer (pM6.1) and Baml-primer (pM6.1$_{-406}$) were used to amplify the N-terminal segment. The Bam2-primer (AAGGATCCACAAGCTAACCCATTCTTCACAG) primed upstream and the Pst-primer (pM6.1) downstream to polymerase the C-terminal segment. The N-terminal fragment was cut with EcoRI/BamHI, the C-terminal segment with BamHI/PstI and both fragments finally cloned into pT7-5 between EcoRI and PstI sites. The plasmid pM6.1$_{ALPSTGE}$ codes for a M6.1 protein that is deleted for its amino acids 407–412 (LPSTGE) and has the amino acids GS substituted between position 403 and 413 of the wild type protein.

Sequences from the phoA gene were amplified from a plasmid which had a 2.7 kb XhoI-Hind III fragment (containing the phoA gene) cloned into pUC8 using the procedure described by Shuttleworth in (10).

pPhoA: The Xba-primer (AATCTAGAGTACATGGAGAAAATAAAG) was utilized as upstream primer and the Pst-primer (TTCTGCAGGTCTGGTTGCTAACAGC) as downstream primer; the amplified fragment was cut with XbaI/PstI and cloned between the corresponding sites of pT7-5. The plasmid pPhoA codes for the whole alkaline phosphatase from *E. coli* K12 strain JM109.

pPhoA:M6.1$_{303-441}$: Amplification was performed upstream with the Xba-primer (pPhoA) and downstream with the Hind1-primer (AAAAGCTTTCAGCCCCAGAGCGGCTTTC). The fragment was digested with XbaI/HindIII. The M6.1$_{303-441}$ fragment was obtained by cutting pVV:M6Δ with HindIII. Both fragments were ligated and cloned into pT7-5 cut XbaI/HindIII. This plasmid expresses a mature protein of 588 amino acids. The first 450 amino acids are PhoA coding sequence and the next 138 are from M6.1 protein, position 303 through 441.

pPhoA:M6.1$_{414-441}$: The Xba-primer (pPhoA) and Hind1-primer (pPhoaA:M6.1$_{303-441}$) generated the PhoA fragment that was XbaI/HindIII digested. The M6 fragment was amplified upstream with the Hind2-primer (AAAAGCTTCAGCTAACCCATTCTTCACAG) downstream with the Pst-primer (pM6.1) and the fragment cut with HindIII/PstI. The PhoA and M6.1 fragments were ligated to pT7-5 digested with XbaI/PstI. This clone has the coding sequences of the whole PhoA protein fused to the hydrophobic domain of M6.1 from position 414-441 at its C-terminus. There is a two amino acid insertion (AS) before the M6.1 region due to the restriction site.

The plasmids pND1 and pND372 are described by Davis et al. (11) Parts of the emm6 gene were fused to the C-terminal part of the pIII gene via the HindIII site of pND372 which opens the reading frame at the codon for amino acid 372, shortly before the membrane anchor of pIII. The pIII constructs were expressed in *E. coli* K561 and HMS174(DE3)(pLysE) with isopropyl-thiogalactoside (IPTG) induction.

pPIII:M6.1$_{367-441}$ pVV:M6 was cut with HinfI, overlapping ends filled with Klenow polymerase and ligated to the HindIII-linker (pCAAGCTTG). The fragment mixture was then cut with HindIII and the appropriate fragment isolated and ligated to pND372. The resulting protein is a fusion of M6.1 from position 367-441 to the C-terminus of pIII at position 372 with a 3 amino acid insertion (PKL) in between due to the HindIII-linker.

pPIII:M6.1$_{413-441}$: The M6 fragment was amplified upstream with the Hind3-primer (AAAAGCTTACAGCTAACCCATTCTTCACAG) and downstream with the Hind4-primer (AAAAGCTTAGAGTTGTTTAGTTTCTGACCTC), digested with HindIII and ligated to pND372. Here the hydrophobic domain of the M6.1 protein from position 413 through 441 is fused to the C-terminus of pIII at position 372, with the same 3 amino acid insertion as pPIII:M6.1$_{367-441}$.

Protein Labeling, Cell Fractionation, and Immunoprecipitation:

Bacteria were grown in the medium described in (12) supplemented with glucose (0.2%) and 19 amino acids as described by Davis et al. (11). *E. coli* K561 and HMS174 (DE3) were grown at 37° C., induced with 2 mM IPTG and the cells harvested after 10 min. induction of the lac promotor. *E. coli* CC118 (pPhoA) and KS476 (pPhoA:M6.1$_{303-441}$ and pPhoA:M6.1414-441) were harvested without induction. The expression proved to be sufficient for labeling experiments. The cell fractionation followed the protocol of Davis et al (11). The cells were pulse labeled with 100 uCi[$^{35}$S] Methionine (New England Nuclear, 1000Ci/mmol) for 50 sec. All proteins were precipitated with trichloroacetic acid to 5%, washed with acetone and dissolved in 25 ul 4% sodium dodecyl sulfate.

Surface Location Experiments

For proteinase accessibility assay, 5 ml of pulse labeled culture was fractionated as described (13) and a sample of periplasm (a) saved. The protoplasts were resuspended in ice cold TSM (50 mM Tris pH8.0, 20% sucrose, and 50 mM MgCl$_2$), equally divided and (b) left unexposed, (c) exposed to 1% Triton X-100, (d) 0.5 ug trypsin, (e) 1% Triton X-100 and 0.5 ug trypsin, (f) 0.5 ug trypsin and 1 ug trypsin inhibitor. Protease digestion was incubated for 30 min on ice. All samples were precipitated with trichloroacetic acid as above, immuno-precipitated, and autoradiographed. This procedure establishes that the M-protein is on the exterior surface of the cellular membrane.

M6 protein and its derivatives were immunoprecipitated with 2 ul of a polyclonal rabbit-serum raised against purified M6 protein (14) per precipitation. Alkaline phosphatase and PhoA:M6 derivatives were precipitated with 3 ul of a polyclonal rabbit serum against bacterial alkaline phosphatase (obtained from 5prime-to-3prime). PIII and its derivatives were precipitated with 0.1 ul of a polyclonal rabbit antiserum. All immunoprecipitation reactions were performed by dissolving 5 ul protein in 200 ul of 1% Triton buffer (150 mM NaCl, 50 mM Tris-HCl, 5 mM EDTA and 1% Triton X-100 pH 7.5) and incubation with the antiserum overnight at 4° C. The immunocomplexes were precipitated the following morning with protein A beads, washed three times with 1% Triton buffer and boiled for 5 min in sample buffer prior to loading on a 12% SDS PAGE. All gels were treated with Enhance (New England Nuclear) and fluorographed with Blue Brand™ (Kodak) films.

Rainbow™ markers (Amersham) were used as protein size standards as follows: myosin, 200 kD; phosphorylase b, 92.5 kD; BSA, 69 kD; ovalbumin, 46 kD; carbonic anhydrase, 30 kD; trypsin inhibitor, 21.5 kD; lysozyme, 14 kD.

The plasmid M6.1$_{367-441}$ is novel. Since it contains LPSTGE, the hydrophobic region and the charged tail of M6, it can be employed to anchor other protein fragments to the cell wall of bacteria. It is, therefore, useful for the production of vaccines. For such utility, the plasmid is fused with a peptide or protein antigen and inserted in a non toxic microbial carrier such as *E. coli*. The protein containing the antigen and the anchoring elements from M6.1$_{367-441}$ will anchor to the surface of the bacterial membrane.

The mammal to be protected is treated e.g., by injection with a vaccine composition including the transformed bacteria. In response, the immunological system generates protective antibodies.

The plasmid has been deposited in *E. coli* strain K561 at the American Type Culture Collection 12301 Parklawn Drive, Rockville, Md., 20852, on May 11, 1990 under the accession number ATCC 68325.

Those skilled in the art will recognize that derivative plasmids of M6.1$_{367-441}$ may also be employed to produce analogs of LPSTGE having anchoring, activity similar to that of LPSTGE. All such plasmid derivatives are included within the scope of this invention.

REFERENCES, ALL OF WHICH ARE INCORPORATED BY REFERENCE

1. Studier, F. W., and B. A. Moffatt. 1986. Use of bacteriophage T7 RNA polymerase to direct selective high-level expression of cloned genes. J. Mol. Biol. 189:113-130.

2. Davis, N. G., J. D. Boeke, and P. Model. 1985. Fine structure of a membrane anchor domain. J. Mol. Biol. 181:111-121.

3. Yarus, M., C. McMillan III, S. Cline, D. Bradley, and M. Snyder. 1980. Construction of a composite tRNA gene by anticodon loop transplant. Proc. Natl. Acad. Sci. U.S.A. 77:5092-5096.

4. Manoil, C., and J. Beckwith. 1985. TnphoA: a transposon probe for protein export signals. Proc. Natl. Acad. Sci. U.S.A. 82-8129-8133.

5. Strauch, K. D., and J. Beckwith. 1988. An *Escherichia coli* mutation preventing degradation of abnormal periplasmic proteins. Proc. Natl. Acad. Sci. U.S.A. 85:1576-1580.

6. Maniatis, T., E. F. Fritsch, and J. Sambrook. 1982. Molecular Cloning. Cold Spring Harbor Laboratory, Cold Spring Harbor.

7. Tabor, S., and C. C. Richardson. 1985. A bacteriophage T7 RNA polymerase/promotor system for controlled exclusive expression of specific genes. Proc. Natl. Acad. Sci. U.S.A. 82:1074-1078.

8. Sanger, F., S. Nicklen, and A. R. Coulson. 1877. DNA sequencing with chain-terminating inhibitors. Proc. Natl. Acad. Sci. USA 74:5463-5467.

9. Hruby, D. E., W. M. Hodges, E. M. Wilson, C. A. Franke, and V. A. Fischetti. 1988. Expression of streptococcal M protein in mammalian cells. Proc. Natl. Acad. Sci. USA 85:5714-5717.

10. Shuttleworth, H., J. Taylor, and N. Minton. 1986. Sequence of the gene for alkaline phosphatase from *Escherichia coli* JM83. Nucl. Acids Res. 14:8689-8689.

11. Vogel, H. J. and D. M. Bonner. 1956. Acetylornithase of *Escherichia coli:* partial purification and some properties. J. Biol. Chem. 218:97-106.

12. Davis, N. G., and P. Model. 1985. An artificial anchor domain: Hydrophobicity suffices to stop transfer. Cell 41:607-614.

13. Fischetti, V. A., K. F. Jones, B. N. Manjula, and J. R. Scott. 1984. Streptococcal M6 protein expressed in *Escherichia coli*. Localization, purification and comparison with streptococcal-derived M protein. J. Exp. Med. 159:1083-1095.

What is claimed is:

1. An isolated and purified DNA encoding a polypeptide, wherein said polypeptide consists of from about six to about twenty amino acid residues and includes as an integral portion of its structure a peptide construct responsible for anchoring a virulence determinant protein to the surface of a gram-positive coccal bacteria wherein the first, second, fourth and fifth amino acid residues of the C-terminal end of said peptide construct are L, P, T, and G respectively.

2. A DNA according to claim 1, wherein said peptide construct has the amino acid sequence LPSTGE.

3. A plasmid vector comprising a DNA of claim 1 operably linked to elements required for its expression of said polypeptide.

4. A plasmid vector according to claim 3, wherein said DNA is further operably linked to a DNA encoding a peptide or protein antigen.

5. A cell transformed with a plasmid vector according to claim 3.

6. The cell of claim 5, wherein said cell is a non-toxic microbial carrier cell.

7. The cell of claim 5, wherein said cell is an *Escheria coli* cell.

8. A composition of matter comprising a DNA according to claim 1 and a carrier therefor.

9. A composition of matter comprising a cell according to claim 5 and a carrier therefor.

10. The plasmid M6.1$_{367-441}$, deposited in *Escherichia coli* strain K561 at the American Type Culture Collection under the accession number ATCC 68325.

11. An isolated and purified DNA encoding a polypeptide, wherein said polypeptide consists of from about six to about twenty amino acid residues and comprises the amino acid sequence L P(x)TG(y), wherein (x) is selected from the group consisting of S, E, T, N, and K, and (y) is selected from the group consisting of E, G, S, and V.

* * * * *

UNITED STATES PATENT AND TRADEMARK OFFICE
CERTIFICATE OF CORRECTION

PATENT NO. : 5,786,205
DATED : July 28, 1998
INVENTOR(S) : Fischetti et al.

It is certified that error appears in the above-indentified patent and that said Letters Patent is hereby corrected as shown below:

Claim 3, (column 12, line 2), delete "its".

Signed and Sealed this

Tenth Day of November 1998

Attest:

BRUCE LEHMAN

Attesting Officer

Commissioner of Patents and Trademarks